United States Patent
Case et al.

(10) Patent No.: US 9,173,762 B2
(45) Date of Patent: Nov. 3, 2015

(54) RETAINING DEVICES, RETAINING DEVICES FOR USE IN RESHAPING EARS AND RELATED SYSTEMS AND METHODS

(71) Applicant: Chondrocyte LLC, Henderson, NV (US)

(72) Inventors: Shilo C. Case, Sandy, UT (US); Gregg D. Niven, Kaysville, UT (US); Pascal Servell, Dallas, TX (US); Jack Savage, Sandy, UT (US)

(73) Assignee: Chondrocyte, LLC, Henderson, NV (US)

( * ) Notice: Subject to any disclaimer, the term of this patent is extended or adjusted under 35 U.S.C. 154(b) by 0 days.

(21) Appl. No.: 14/385,980

(22) PCT Filed: Mar. 15, 2013

(86) PCT No.: PCT/US2013/032182
§ 371 (c)(1),
(2) Date: Sep. 17, 2014

(87) PCT Pub. No.: WO2013/142342
PCT Pub. Date: Sep. 26, 2013

(65) Prior Publication Data
US 2015/0051639 A1 Feb. 19, 2015

Related U.S. Application Data

(60) Provisional application No. 61/613,358, filed on Mar. 20, 2012.

(51) Int. Cl.
A61F 11/00 (2006.01)
A61F 5/01 (2006.01)

(52) U.S. Cl.
CPC ............... *A61F 5/0102* (2013.01); *A61F 5/01* (2013.01); *A61F 11/004* (2013.01); *A61F 2220/0008* (2013.01)

(58) Field of Classification Search
CPC ..... A61F 5/0102; A61F 11/00; A61F 11/004; A61F 11/06; A61F 11/14
USPC ........ 606/151, 204.15; 602/53, 61, 74; 2/209, 2/423; 623/10
See application file for complete search history.

(56) References Cited

U.S. PATENT DOCUMENTS 4,187,838 A    2/1980 Dubrowski
4,850,055 A *  7/1989 Hwang ............................. 2/209

(Continued)

FOREIGN PATENT DOCUMENTS

CA    1078690    6/1980
JP    10014971   1/1998

(Continued)

OTHER PUBLICATIONS

Auri Clinic, website printout, 1 page, http://shop.auriclinic.com/index.php?language=en, visited Oct. 29, 2009.

(Continued)

*Primary Examiner* — Kathleen Holwerda
(74) *Attorney, Agent, or Firm* — Brian C. Trask (57) ABSTRACT

Retaining devices for use with ears of a subject may include a first portion configured to be secured to a subject's head and a second portion configured to position the helix of the subject's ear. Methods of reshaping tissue of a subject's ear may include performing a laser treatment on the tissue of the subject's ear and installing a retaining device on the subject's ear.

17 Claims, 10 Drawing Sheets

(56) References Cited

U.S. PATENT DOCUMENTS

| | | |
|---|---|---|
| 5,295,950 A | 3/1994 | Godley |
| 5,775,336 A | 7/1998 | Morris |
| 6,517,557 B1 | 2/2003 | Sorribes |
| 6,626,945 B2 | 9/2003 | Simon et al. |
| 6,632,246 B1 | 10/2003 | Simon et al. |
| 6,852,125 B2 | 2/2005 | Simon et al. |
| 7,025,061 B2 | 4/2006 | Haussmann |
| 7,069,745 B1 | 7/2006 | Finley |
| 7,093,600 B2 | 8/2006 | Sorribes |
| 7,117,546 B2 * | 10/2006 | Goulding .......................... 2/423 |
| 7,153,313 B2 | 12/2006 | Whitton |
| 7,850,702 B2 | 12/2010 | Sorribes et al. |
| 8,113,208 B2 | 2/2012 | Chaisson et al. |
| 8,491,510 B2 | 7/2013 | Byrd et al. |
| 8,627,824 B2 * | 1/2014 | Koehler ....................... 128/858 |
| 2001/0039455 A1 | 11/2001 | Simon et al. |
| 2004/0039447 A1 | 2/2004 | Simon et al. |
| 2004/0162622 A1 | 8/2004 | Simon et al. |
| 2006/0042640 A1 | 3/2006 | Haussmann |
| 2008/0195216 A1 | 8/2008 | Philipp |
| 2009/0030358 A1 | 1/2009 | Byrd et al. |
| 2010/0204793 A1 | 8/2010 | Byrd et al. |
| 2011/0266265 A1 | 11/2011 | Lang |
| 2012/0226307 A1 | 9/2012 | Servell et al. |

FOREIGN PATENT DOCUMENTS

| | | |
|---|---|---|
| JP | 4431066 | 3/2010 |
| WO | 0191672 | 12/2001 |
| WO | 2009014908 | 1/2009 |
| WO | 2011/129900 | 10/2011 |
| WO | 2013/142342 | 9/2013 |

OTHER PUBLICATIONS

Earwell TM Infant Ear Correction System, Brochure, Becan Medical Limited, Tucson, Arizona, 2008.

Leclere et al., Laser-Assisted Cartilage Reshaping (LACR) for Treating Ear Protrusions: A Clinical Study in 24 Patients, Aesth Plast Surg. May 30, 2009, published online by Springer.

Mordon et al., Laser Cartilage Reshaping in an In Vivo Rabbit Model Using a 1.54 f.!m Er:Giass Laser, Lasers Surg. Med. 2004, pp. 315-322, vol. 34.

Mordon et al., Correction of ear malformations by Laser Assisted Cartilage reshaping (LACR): a preliminary study in 10 patients, Lasers Surg. Med. 2006, pp. 659-662, vol. 38 No. 7.

PCT International Search Report and Written Opinion, PCT/US2013/032182 dated Jul. 10, 2013.

PCT International Search Report and Written Opinion, PCTUS2011/000688 dated Jan. 17, 2012.

Sorribes, et al., Nonsurgical Treatment of Prominent Ears With the Auri Method, 2002, pp. 1369-1376, vol. 28.

Extended European Search Report and Written Opinion, PCT/US2011000688, P99789EP00, mailed Feb. 26, 2015.

* cited by examiner

RETAINING DEVICES, RETAINING DEVICES FOR USE IN RESHAPING EARS AND RELATED SYSTEMS AND METHODS

CROSS-REFERENCE TO RELATED APPLICATION(S)

This application is the national phase entry of PCT/US2013/032182, filed Mar. 15, 2013, published in English as WO 2013/142342 A1 on Sep. 26, 2013, which claims the benefit under Article 8 of the PCT and 35 U.S.C. §119(e) of the filing date of U.S. Patent Application Ser. No. 61/613,358, filed Mar. 20, 2012, for "RETAINING DEVICES, RETAINING DEVICES FOR USE IN RESHAPING EARS AND RELATED SYSTEMS AND METHODS," the disclosure of which is hereby incorporated herein in its entirety by this reference.

TECHNICAL FIELD

The disclosure generally relates to medical devices and related systems and methods. In particular, embodiments hereof relate to retaining devices and related systems and methods for reshaping tissue, such as human or mammalian ears and methods of reshaping ear including retaining devices.

BACKGROUND

Ear deformations affect 5% of the Caucasian and Latino population or 12.1 million people (5% of 242.3 million). Each year, 4.26 million children are born of white or Latino parents (2.3 million whites and 1 million Hispanics). Of these, approximately 165,000 are born with deformed ears.

However, according to the American Society of Plastic Surgeons (ASPS), only 29,434 cosmetic ear surgery procedures were performed last year in the US and these were primarily performed on children, leaving the vast majority of the population untreated (it is interesting to note that otoplasty is the only cosmetic procedure performed on children, testifying to the damaging psychological issues stemming from this condition).

The average child has 85% ear development by 3 years of age and ears are typically fully grown by the age of 7 years (the height continues to grow into adulthood, but the width and distance from ear to scalp changes little). This fact in part explains why this procedure is popular with children, as procedures performed from this age onwards will yield permanent results.

Ears also have surprisingly similar features in terms of size, protrusion from the scalp and angle from the cranium. The following is a list of considered standard sizes: fully grown ears protrude from the scalp about 1.8-2.0 cm at midpoint; ear length is typically 5.5-6.5 cm; ear width is typically 3.0-4.5 cm; the ratio between width and length is about 50% to 60%; helical Rim (Helix) 7 mm or about 10% of the height; ear vertical axis 15 to 30 degrees posterior (with the top further back than the bottom).

Features constituting what is considered "normal" ear features are: scapha angle greater than 90 degrees; conchal bowl height less than 1.5 cm; and angle head to ear: female less than 21 degrees and male less than 25 degrees.

Ear deformations typically fall into two broad categories, cartilage deformations and non-cartilage related deformations. Cartilage deformations include prominent (or bat) ears which typically is a problem either of an oversized concha, or too wide an antihelical fold angle or a combination of the two; helical deformations that include: constricted ear including hooding or folding of the helical rim; lop ear where the top of the ear is folded down and forward; cup ear including malformed protruding ear with the top folded down and a large concha; shell ear where curve of the outer rim as well as the folds and creases are missing; and stahl's ear (Spock's ear) where there is an extra fold and pointed top. Non-cartilage related deformations include: lobe deformations, macrotia (oversized ears), and microtia (undersized ears).

Surgical Ear Correction: Otoplasty

The first otoplastic technique to correct protruding ears is attributed to Ely in 1881. Since that report, over 180 surgical techniques have been described in the literature for the correction of protruding ears. These techniques can be subdivided into 3 sub-groups:

"Suture only" technique: First described by Furnas in 1968 (and still used to this day), this technique is used primarily to set back the ears and involves retracting the skin behind the ear and place 2-3 non-resorbable sutures to retract the position of the ear. The Mustarde method is today the most common.

Cartilage splitting or weakening technique or "Davis" method: Excision of skin and cartilage to correct conchal hypertrophy.

Combination of the above two or "converse Wood-Smith" technique: uses a cartilage cutting and suture method to correct and create an anti-helical fold.

All these surgical techniques tend to be performed on an outpatient basis under sedation, although when dealing with children it is advisable to perform it under general anesthesia. The procedure is generally performed primarily by Facial Plastic Surgeons and, to a lesser extent by Dermatologists, ENT and Maxillofacial Surgeons. It typically takes 2 to 3 hours to perform and is not without risks.

Major complications from corrective ear surgery may occur and can be divided into two categories: immediate complications: hematoma and infection which may result in necrosis; and long-term complications include hypertrophic (keloid) scars, loss of sensitivity (resulting from damage to nerve endings), skin and cartilage necrosis as well as unaesthetic results or recurrence of the ear deformity. These complications are responsible for the high (10%) rate of repeat surgeries.

SUMMARY OF THE DISCLOSURE

Described are retaining devices and related systems and methods for reshaping tissue (e.g., cartilage structures), such as a human or mammalian ear and methods of reshaping ear including retaining devices.

Disclosed is a retaining device for use with an ear of a subject including a first portion configured to be secured to a subject at a location between a helix of the ear of the subject and a portion of the subject's head (e.g., by double sided adhesive tape) and a second portion configured to position the helix of the subject's ear.

In some embodiments, the first portion and the second portion are coupled by a hinge portion.

In some embodiments, the hinge portion may bias the first portion in a direction toward the second portion.

Also disclosed is a retaining device for use with an ear of a subject including a base portion configured to affix to a subject at a location between a helix of the ear of the subject and a portion of the subject's head, a spacer portion configured to space the subject's ear from the subject's head, and a retainer portion configured to position and retain the helix of the subject's ear.

Further disclosed is a retaining device system for reshaping at least one ear of a subject including at least one base portion configured to affix to the subject's head; at least one interchangeable spacer portion configured to couple to the base portion and configured to space the subject's ear from the subject's head; and a plurality of interchangeable retainer portions configured to couple to at least one of the spacer portion and the base portion and configured to position and retain the helix of the subject's ear.

In certain embodiments, disclosed is a method of reshaping tissue of a subject's ear. The method including performing a laser treatment on the tissue of the subject's ear and installing a retaining device on the subject's ear.

MODE(S) FOR CARRYING OUT THE INVENTION

In the following detailed description, reference is made to the accompanying drawings that depict, by way of illustration, specific embodiments in which the disclosure may be practiced. However, other embodiments may be utilized, and structural, logical, and configurational changes may be made without departing from the scope hereof. The illustrations presented herein are not necessarily meant to be actual views of any particular material, apparatus, assembly, system, or method, but are merely generally idealized representations that are employed to describe various embodiments. The drawings presented herein are not necessarily drawn to scale. Additionally, elements common between drawings may retain the same numerical designation.

Generally, the retaining device described herein is used to support and retain human tissues such as the ear. For example, the retaining device may be used to retain a portion of a subject's ear in order to alter the shape of the subject's ear. For example, the retaining device may be used to alter the shape of a subject's ear that exhibit an angle exceeding 20 to 30 degrees between the ear (e.g., the helix of the ear) or the shape of a subject's ear that are hooded (i.e., folding of the helical rim of the ear).

In some embodiments, the retaining device may support and retain treated tissues of the ear (e.g., laser treatment) in "normal" angles, forms, and shapes. For example, a physician may treat the tissue of the ear per the methodology described in World Intellectual Property Organization (WIPO) Publication WO 2011/129900 A2, published Oct. 20, 2011, the disclosure of which is incorporated in its entirety by this reference. The ear may be supported and retained in positions that displace the ear into configuration considered standard as discuss above or in any other desired configuration, cosmetic or otherwise (e.g., as determined by the subject and physician during the consultation).

In some instances, each type of treatment involving reshaping of a subject's ear may have specific needs, such as the special support, torque, unfolding, spacing, and angle creation that is unique to the tissue of the deformity of shape. Further, some cases might require a combination of support structures possibly consisting of unique retention needs as well as various spacing needs. Accordingly, some embodiments of the retaining device may be flexible (e.g., scalable, modular, and/or modifiable) in design to enable a wide variety in reshaping options by varying the size and configuration of the various parts of the retaining device. For example, the design of the retaining device may address a majority of by being scalable (e.g., available in a variety of sizes to address the various reshaping needs of each subject. Further, the various size and/or parts of the retaining device may be chosen and are determined by the physician at the time of the exam. In some embodiments, the chosen parts of the retaining device may be easily assembled and placed in position during the growth of the cartilage. In some embodiments, the various parts may be modified as necessary.

In some embodiments, the retaining device may comprise one or more portions that are movable and/or adjustable relative to one another in order to enable a practitioner to fit the retaining device to a majority of subjects' ears. For example, the retaining device may include a hinged portion enabling a portion of the retaining device that fits over the subject's helix to be rotated relative to a base portion that is attached to the subject's head. Such movement may enable a practitioner to easily install and remove the retaining device and, in some embodiments to adjust the fit of the retaining device on the subject's ear.

In addition to the various support needs of the above deformities, ear tissue of each subject comes in a variety of sizes and shapes. Some embodiments of the retaining device may be easily scalable to provide multiple sizes of retaining devices that may be selected based on the configuration of subject's ear and/or the treatment selected. Further, some embodiments of the retaining device may enable the structure of the retaining device to be adjusted and/or customized on a case-by-case basis to fit the required needs of support, retention, and spacing during the reshaping process. Proper selection and choice of the retaining device features will enable a successful treatment results for the subject.

In some embodiments, the retaining device or components thereof may be sized for an optimal fit to the physical properties of the subject ear, which include size or height of the sulcus measured vertically, the curvature of the sulcus, and the desired finished angle measured between the skull and the rear of the helix. For example, the physician at the time of an examination of the ear may perform measurements of the subject's ear. The sulcus may be measured to determine the overall height of the retaining device. The sulcus is the crease of tissue that lies at the junction of the back of the ear and the surface of the skull tissue. The shape of the sulcus includes a complex curved pattern that may be described as a combination of swept curves of arcs joined tangentially at the ends. The sulcus will be measured for height to best fit the height of the retaining device for comfort and best support and also for the projection of depth of the curvature, also for best comfort and support of the forming tissues.

The angle of the helix may also be measured to determine the choice for the parts of the retaining device, which will retain and hold the tissue during growth. This angle will generally fall between 15 to 20 degrees when measured between the side of the head and the face of the ear consisting of a plane described by the helix and base of the ear near the auditory canal. The angle and resultant selection of parts for the retaining device may also be determined by what the subject desires the finished angle to be upon conclusion of the treatment.

It is believed that measurements of subjects' ears will generally fall into several general common sets or sizes based upon the shape of the general population of ears. Accordingly, providing embodiments of the retaining device disclosed herein a several sizes may enable treatment of a majority of subjects. However, if the sizes of or combination of required parts based upon the measurements of the subject ear, fall outside the normal set of common assemblies, new combination sets or custom sized sets of parts for the retaining device may be fabricated or existing sets may be modified.

Figure 1:
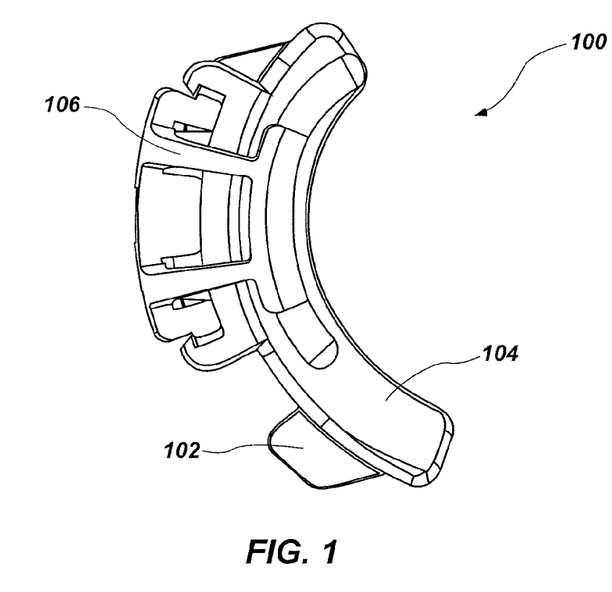
FIG. 1 illustrates a side view of a retaining device in accordance with an embodiment of the present disclosure.
Figure 2:
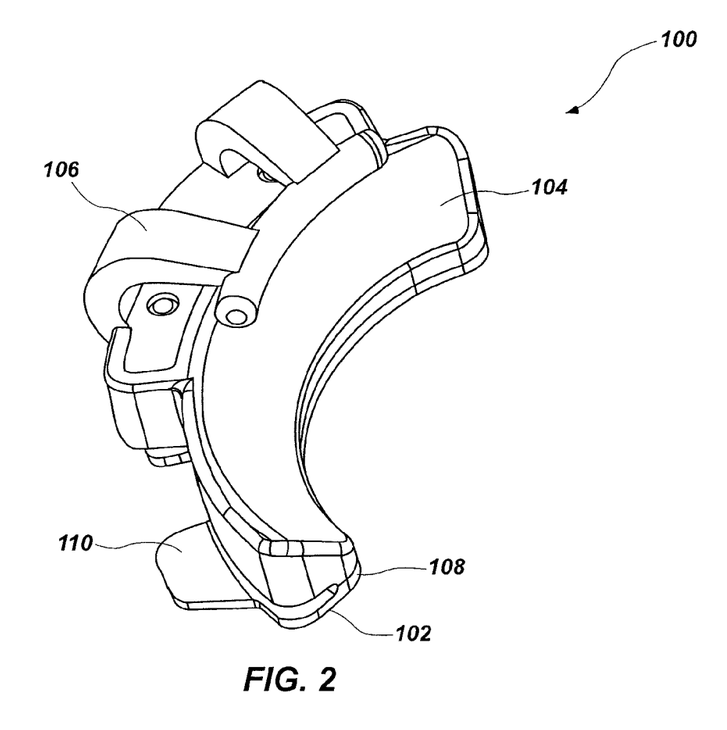
FIG. 2 illustrates a perspective view of the retaining device shown in FIG. 1.

FIGS. 1 and 2 illustrate a side view and a perspective view, respectively, of a retaining device in accordance with an embodiment of the present disclose. As shown in FIGS. 1 and 2, the depicted retaining device 100 includes a portion for retaining the ear and one or more portions for spacing the ear from the subject's head and/or securing the retaining device 100 to the subject's head. For example, the retaining device 100 may include a base portion 102, a spacer portion 104, a retainer portion 106, and, optionally, an adhesive portion. In some embodiments, the base portion 102, the spacer portion 104, and the retainer portion 106 may be formed by two or more components enabling customization and variability of the retaining device as discussed above. For example, the base portion 102, the spacer portion 104, and the retainer portion 106 may each be formed as separate components that are selected by size and configuration to form a retaining device 100 having the desired fit for each subject. Such size and combination of components may be selected by the physician at the time of treatment to provide optimal support and retention for the subject ear, for example, during the period of cartilage growth. The components may be joined (e.g., permanently joined, semi-permanent joined or removably joined, or combinations thereof) to enable flexibility and custom fitting for each subject's size and treatment requirement. For example, the base portion 102 and the spacer portion 104 may be joined together (e.g., with an adhesive) and the retainer portion 106 may be removably coupled to the base portion 102 and the spacer portion 104 (e.g., by a fastener, interference fit, combinations thereof, etc.). In other embodiments, the entire retaining device 100 or portions thereof (e.g., the base portion 102 and the spacer portion 104) may be formed as a unitary structure.

In some embodiments, one or more portions of the retaining device 100 may be formed from materials such as, for example, thermoplastic resin, lightweight metal alloys, or combinations thereof in a casting or molding process. After casting or molding, portions of the retaining device 100 (e.g., the base portion 102, the spacer portion 104, the retainer portion 106 or combinations thereof) may be refined through processes such as, for example, by altering the shape and positioning of portions of the retaining device 100 and/or by removing material from portions of the retaining device 100 (e.g., by a machining process or an ultrasonic process such as an ultrasonic bath).

Figure 3:
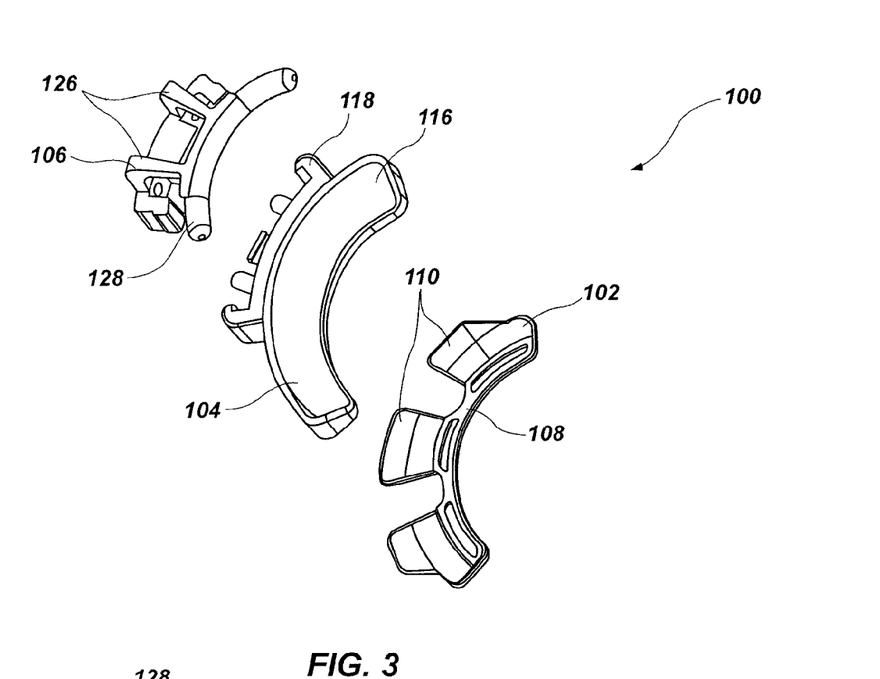
FIG. 3 illustrates an exploded view of the retaining device shown in FIG. 1.
Figure 4:
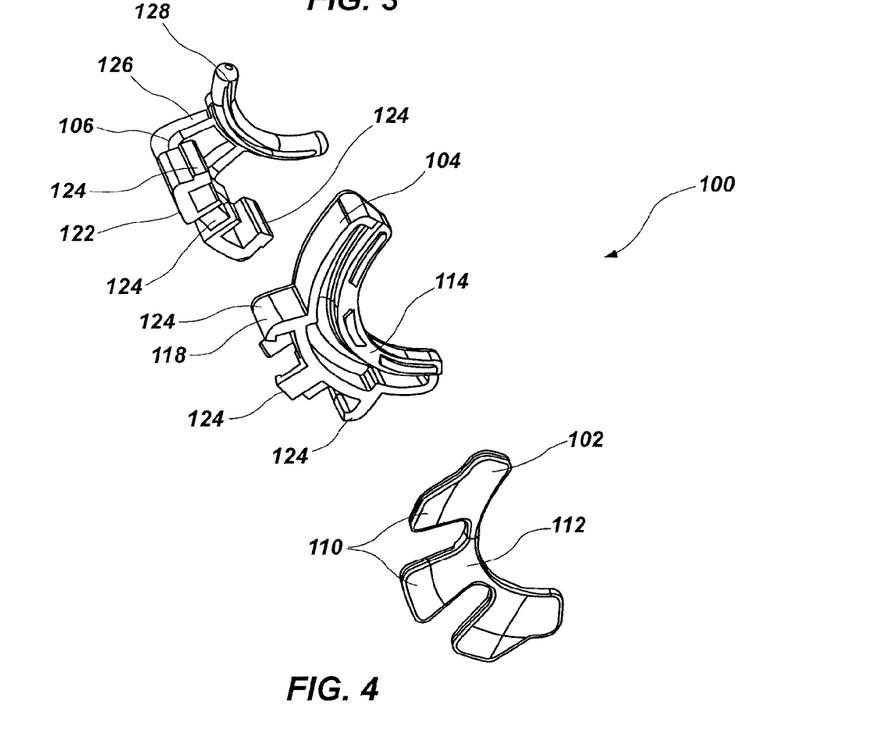
FIG. 4 illustrates another exploded view of the retaining device shown in FIG. 1.
Figure 5:
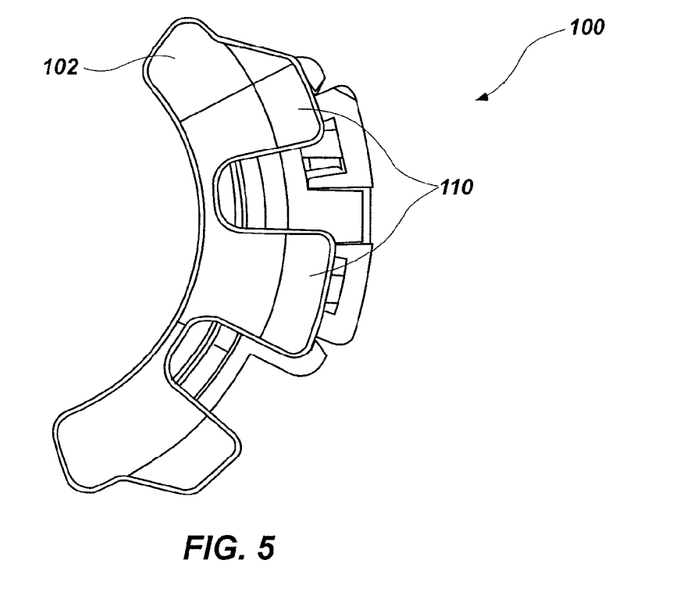
FIG. 5 illustrates another side view of the retaining device shown in FIG. 1.
Figure 12:
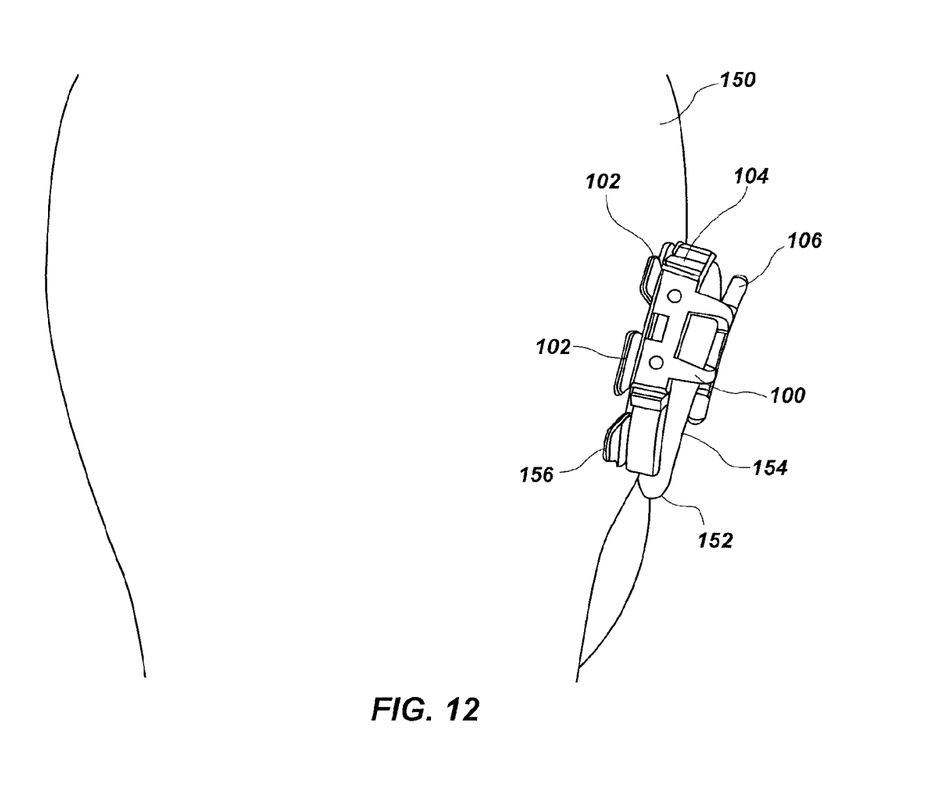
FIG. 12 illustrates another view of the retaining device in use with the ear of the subject as shown in FIG. 11.
Figure 13:
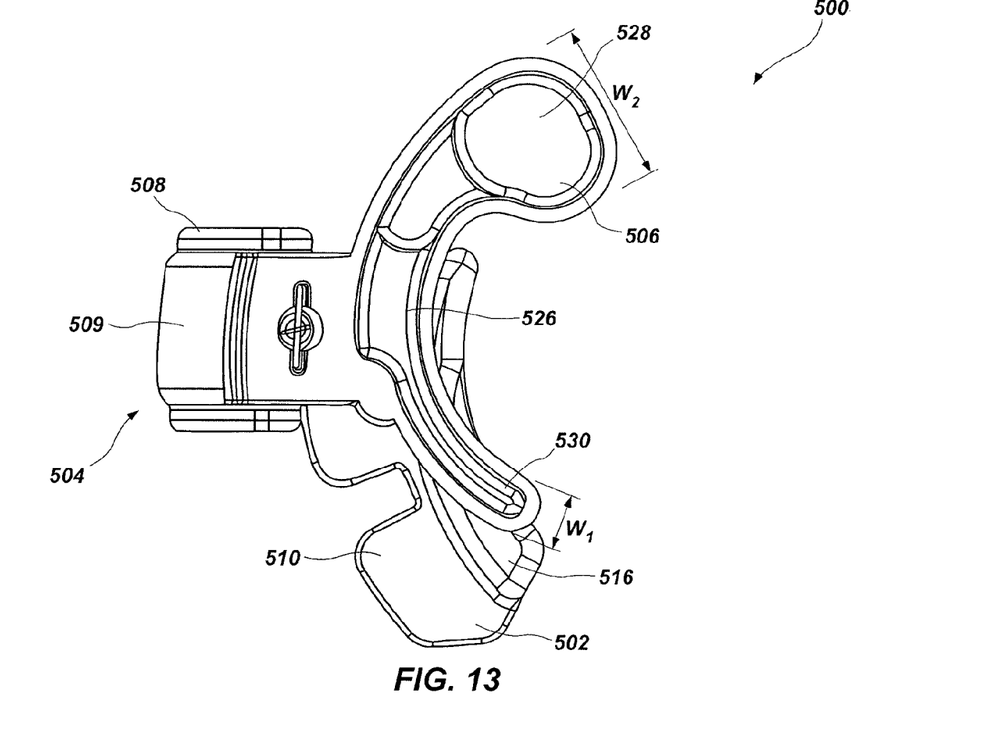
FIG. 13 illustrates a side view of a retaining device in accordance with another embodiment of the present disclosure.
Figure 14:
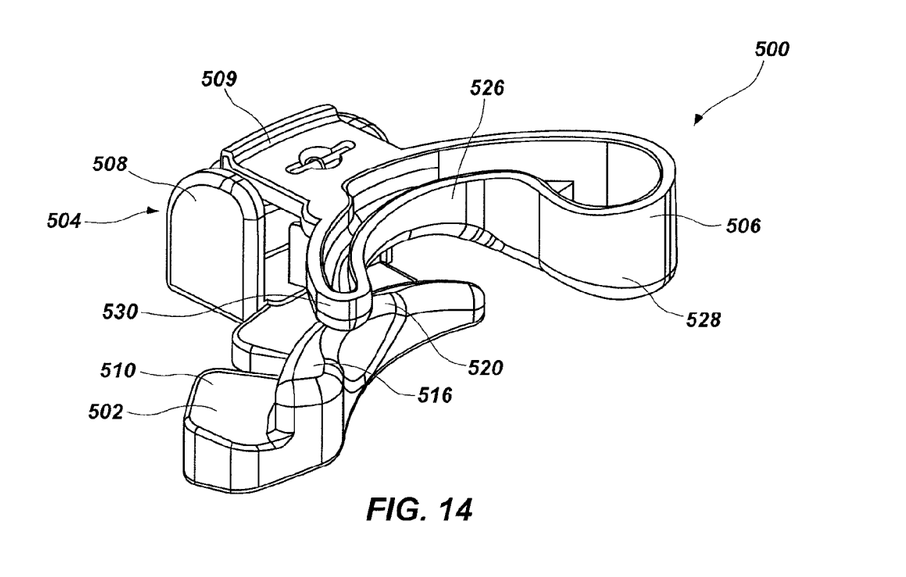
FIG. 14 illustrates a perspective view of the retaining device shown in FIG. 13.
Figure 15:
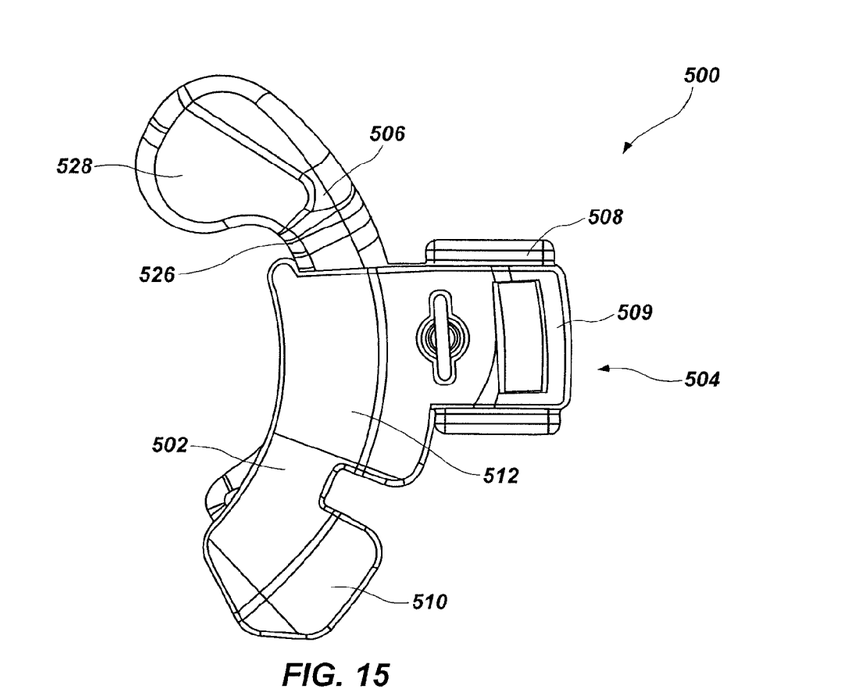
FIG. 15 illustrates another side view of the retaining device shown in FIG. 13.

As shown in FIGS. 3 and 4, which illustrate exploded views of the retaining device 100 and FIG. 5, which illustrates a side view of the retaining device 100, the base portion 102 of the retaining device 100 may be formed to fit a shape of the skull (i.e., head) of a subject proximate the ear (e.g., proximate the sulcus or the connection of the ear to the subject's head (see, e.g., FIG. 12). For example, the base portion 102 may be formed as a substantially curved shape. The base portion 102 may include a connection portion 108 for coupling with the spacer portion 104. The connection portion 108 may be formed on an inner portion of the curved base portion 102 such that the base portion 102 contacts the spacer portion 104 only along an inner portion (e.g., a radially inner portion) of the spacer portion 104 (see FIG. 2). Stated in another way, the base portion 102 and the spacer portion 104 may be coupled only along an inner portion thereof such that an outer portion of the base portion 102 is spaced from an outer portion of the spacer portion 104. The inner portion of the spacer portion 104 may be designed to fit complex curvature of the sulcus. The base portion 102 may include one or more tabs 110 extending radially outward from the inner portion of the base portion 102 (e.g., at equal intervals along the base portion 102) to form an outer portion of the base portion 102. Portions of the base portion 102 (e.g., the tabs 110 and the connection between the base portion 102 and the spacer portion 104 at the inner portion) may enable the base portion 102 to flex in order to conform to any irregularities of the skull surface, while providing a secure mounting surface 112 for the retaining device 100. For example, the base portion 102 may enable the retaining device 100 to be secured to head of the subject by the use of an adhesive. A portion of the tabs 110 may be smoothed out (e.g., rounded at the distal ends) to prevent the base portion 102 from irritating skin surfaces around the ear.

The spacer portion 104 may be formed as a substantially curved shape to be substantially coextensive with the base portion 102 and may be formed to fit a portion of the subject (e.g., the sulcus of the subject's ear). The spacer portion 104 may include a connection portion 114 on an inner portion of the spacer portion 104 for coupling with the base portion 102. The spacer portion 104 may include a support surface 116 for supporting a portion of the ear (e.g., the helix). The spacer portion 104 may include a connection portion 118 for coupling with (e.g., removably coupling) the retainer portion 106.

Figure 6:
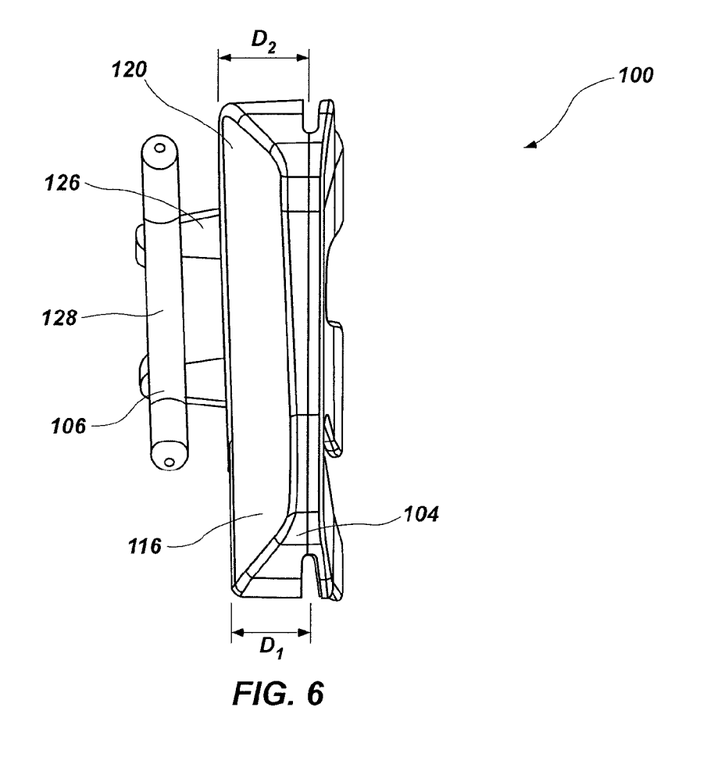
FIG. 6 illustrates a front view of the retaining device shown in FIG. 1.

As shown in FIG. 6, the spacer portion 104 may be sized to orient the ear in a desired position. For example, the thickness of the spacer portion 104 may be varied along its length (e.g., vertical length in the orientation shown in FIG. 6). The spacer portion 104 may include a lower portion (e.g., a portion configured to be positioned proximate to the lobules of the ear) having a first thickness $D_1$ and an upper portion (e.g., a portion configured to be positioned proximate to the cymba concha of the ear or the apex of the helix) having a second thickness $D_2$. The spacer portion 104 may be configured such that second thickness $D_2$ is greater than the first thickness $D_1$, thereby forming an angled side surface 120 of the spacer portion 104 opposite the interface between the spacer portion 104 and the base portion 102. The support surface 116 may be formed by a chamfer on the angled side surface 120 to hold and set the helix of the ear at a desired angle. The support surface 116 of the spacer portion 104 may be placed against the outside of the concha and under the helix (i.e., between the ear and head of the subject) providing support and angle control for the helix. When the retaining device 100 is in position, the tissue of the ear may be in contact with the spacer portion 104 (e.g., the support surface 116) without pushing or applying torque to the tissue of the ear. The combination of the base portion 102 and spacer portion 104 may encourage proper placement for the retaining device 100 (or components thereof) and support the ear tissues in the desired healing position for the treatment.

As mentioned above, in some embodiments, the base portion 102 and spacer portion 104 may be permanently attached together (e.g., by means of solvent adhesives, with an ultrasonic joint or thermal joint, etc.) to ensure secure attachment at the connection portions 108, 114 (FIGS. 3 and 4).

Figure 7:
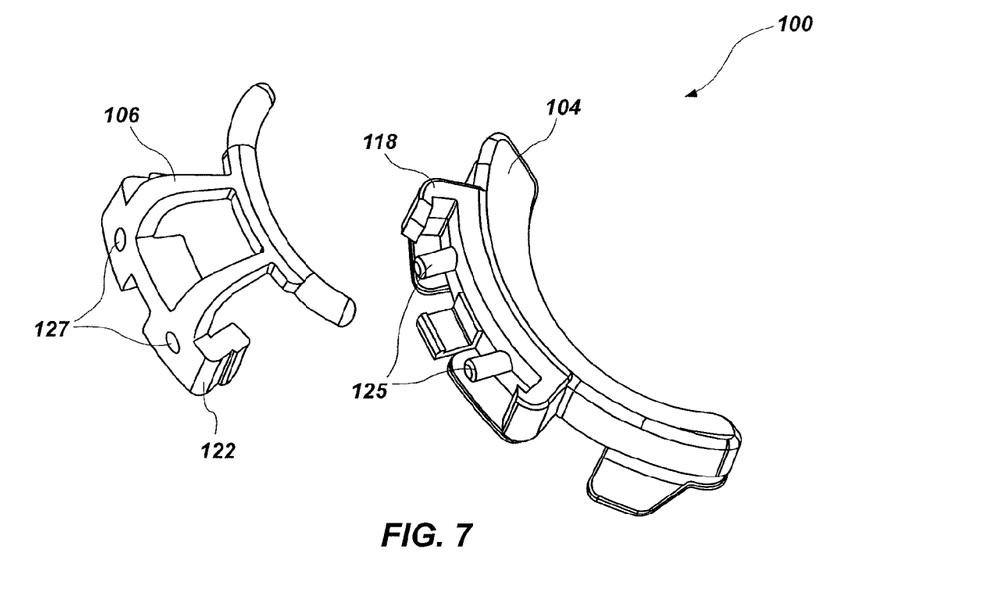
FIG. 7 illustrates yet another exploded view of the retaining device shown in FIG. 1.

Referring again to FIGS. 3, 4, and 6, the retainer portion 106 may be configured to retain a portion of the subject's ear (e.g., the helix). For example, the retainer portion 106 may retain the helix proximate to (e.g., against and in contact with) the spacer portion 104 (e.g., the support surface 116). The retainer portion 106 may include a connection portion 122 for coupling to the connection portion 118 of the spacer portion 104. As discussed above, the retainer portion 106 may removably connect to another portion of the retaining device 100 (e.g., the spacer assembly 104). For example, the retainer portion 106 may be designed to be attached by the physician to one or more of the base portion 102 and the spacer portion 104. This may enable the physician to tailor the shape of the retainer portion 106 or to select from a plurality of retainer portions 106 having different configurations and sizing to meet the individual needs of each subject's ears throughout a reshaping process. In some embodiments, the connection portions 118, 122 of the spacer portion 104 and the retainer portion 106 may include one or more interlocking members 124 (e.g., on or more latches or tabs and complementary receiving portions) to secure the spacer portion 104 to the retainer portion 106. In other embodiments, the connection portions 118, 122 may comprise any suitable configuration to secure the spacer portion 104 and the retainer portion 106 (e.g., undercuts, snap fits, pins, screws and mating holes, one or more adhesive surfaces, etc.). For example, and as shown in FIG. 7, the connection portion 118 of the spacer portion 104 of the retaining device 100 may include one or more protrusion 125 that may be received in complementary apertures 127 of the connection portion 122 of the retainer portion 106.

Referring still to FIGS. 3, 4, and 6, the retainer portion 106 may include one or more arms 126 supporting a retainer 128 that extend from the connection portion 122. The arms 126 may be configured to extend around at least a portion of the helix of the ear of a subject (e.g., the arms 126 may be substantially L-shaped or J-shaped). The arms 126 may also be configured to position the retainer 128 at a position offset from spacer portion 104. For example, the arms 126 may position the retainer 128 such that a portion of the helix of the subject's ear may be received between the spacer portion 104 (e.g., the support surface 116) and the retainer 128.

The retainer 128 may be formed to extend along at least a portion of the helix of the subject in order to position and retain the helix. For example, the retainer 128 may be formed as a substantially curved shape to be substantially coextensive with at least a portion of the base and spacer portions 102, 104 and/or a portion of the helix.

As above, the retainer portion 106, arms 126, and retainer 128 may be formed to enable the positioning and configuration thereof to be modified in order to customize the fit of the retaining apparatus 100 on each subject. For example, the arms 126 and retainer 128 may be altered (e.g., by bending portions of the retainer portion 106 during a thermal and/or ultrasonic process) to customize the spacing between the retainer 128 and the spacer portion 104 or to customize the curvature of the retainer 128.

It is noted that while the embodiment of FIG. 6 illustrates the retainer portion 106 as having arms 126 and retainer 128, the retainer portion 106 may comprise any configuration desirable to retain and position a portion of the subject's ear. For example, the retainer portion 106 may comprise a plurality of tabs, a wire, or combinations thereof extending from the spacer portion 104 (e.g., as shown in FIGS. 7 through 10).

Figure 8:
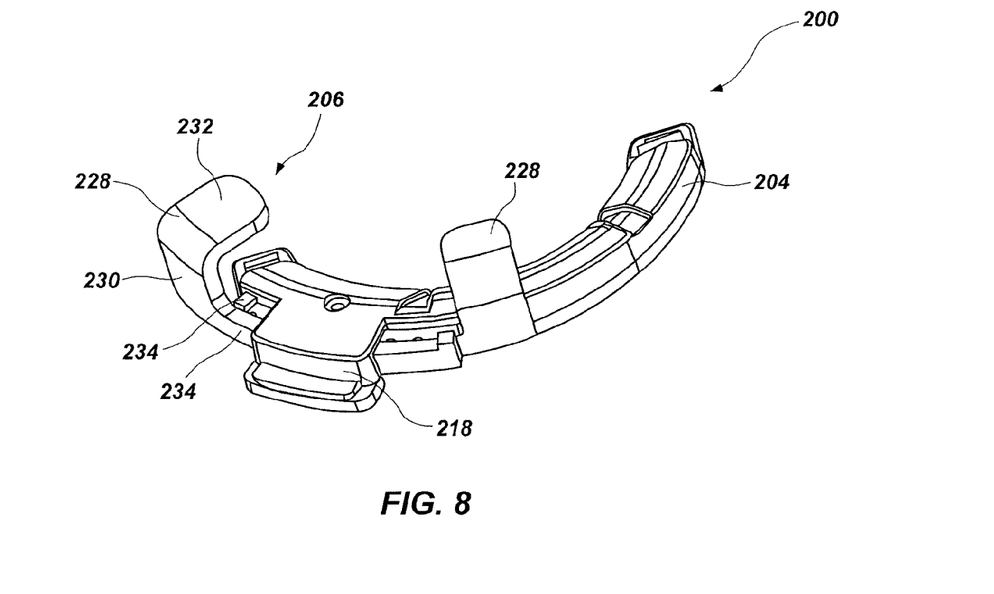
FIG. 8 illustrates a perspective view of a retaining device in accordance with another embodiment of the present disclosure.

FIG. 8 illustrates a retaining device in accordance with another embodiment of the present disclosure. In some embodiments, retaining device 200 may be somewhat similar and include any of the various components of retaining device 100 discussed above with reference to FIGS. 1 through 7. As shown in FIG. 8, retaining device 200 may include a retainer portion 206 have one or more discrete retainers 228 having a substantially J-shape or L shape with an extension 230 and a cantilever 232. The retainers 228 may extend form a spacer portion 204 and are configured to hold a portion of the subject's ear in a selected position (e.g., against a support surface of the spacer portion 204.

In some embodiments, the retainers 228 may be movably coupled to the spacer portion 204. For example, the retainers 228 may include slidable arms 234 that slide along an outer portion of circumference of the spacer portion 204. The sliding retainers 228 may be adjustable along the outer portion of the spacer portion 204 such that the retainers may be positioned at variable positions along the helix of a subject. After being positioned at desired locations, the sliding retainers 228 may be secured in position with a connection portion 218 between the spacer portion 204 and the retainer portion 206.

Figure 9:
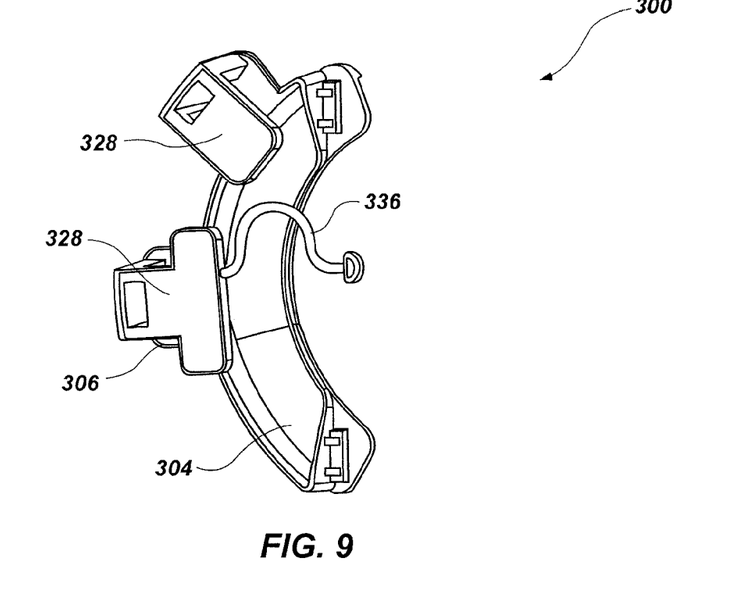
FIG. 9 illustrates a perspective view of a retaining device in accordance with yet another embodiment of the present disclosure.

FIG. 9 illustrates a retaining device in accordance with yet another embodiment of the present disclosure. In some embodiments, retaining device 300 may be somewhat similar and include any of the various components of retaining devices 100, 200 discussed above with reference to FIGS. 1 through 8. As shown in FIG. 9, retaining device 300 may include a spacer portion 304 and a retainer portion 306 including one or more discrete retainers 328 similar to those described above with reference to FIG. 8. The retaining device 300 may include an element configured to apply a force against a portion of the subject's ear extending from a portion of the retaining device 300 (e.g., one or more of the retainers 328). For example, a wire 336 (e.g., a plastic molded cantilevered spring, a wire covered in a plastic sheath, or combinations thereof) may extend from one of the retainers 328 (e.g., in a direction toward the concha). The wire 336 may apply a rotational force (e.g., torque) against tissue of the ear (e.g., the helix, the antihelix, or combinations thereof) to further position the ear in the desired position.

Figure 10:
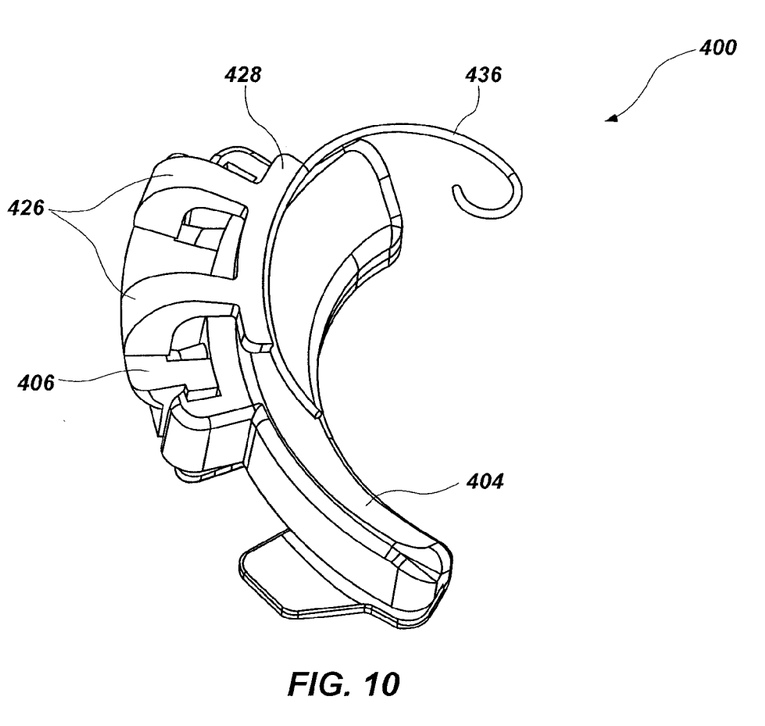
FIG. 10 illustrates a perspective view of a retaining device in accordance with yet another embodiment of the present disclosure.

FIG. 10 illustrates a retaining device in accordance with yet another embodiment of the present disclosure. In some embodiments, retaining device 400 may be somewhat similar and include any of the various components of retaining devices 100, 200, 300 discussed above with reference to FIGS. 1 through 9. As shown in FIG. 10, retaining device 400 may include a spacer portion 404 and a retainer portion 406 including a retainer 428 supported by arms 426 similar to those described above with reference to FIGS. 1 through 7. Similar to retaining device 300, retaining device 400 may include an element configured to apply a force against a portion of the subject's ear extending from a portion of the retaining device 400 (e.g., the retainer 428). For example, a wire 436 (e.g., a plastic molded cantilevered spring, a wire covered in a plastic sheath, or combinations thereof) may extend from the retainer 428. The wire 436 may, for example, extend and curve along the retainer 428 and along a portion of the helix. The wire 436 may apply a rotational force (e.g., torque) against tissue of the ear (e.g., the helix) to further position the ear in the desired position.

As above, the retainer portion 206, 306, 308, arms 426, retainers 228, 328, 428, and wires 336, 436 may be formed to enable the positioning and configuration thereof to be altered in order to customize the fit of the retaining device 200, 300, 400 on each subject. For example, to reshape the ear by holding the helix back to a 15 to 20 degree angle between the helix and the skull of the subject. In some embodiments, a malleable wire (e.g., wires 336, 436) may enable the physician to bend the wire form into a customized form to capture the undulations and changing surfaces of the helix, anti-helix, or other forms of the ear.

Figure 11:
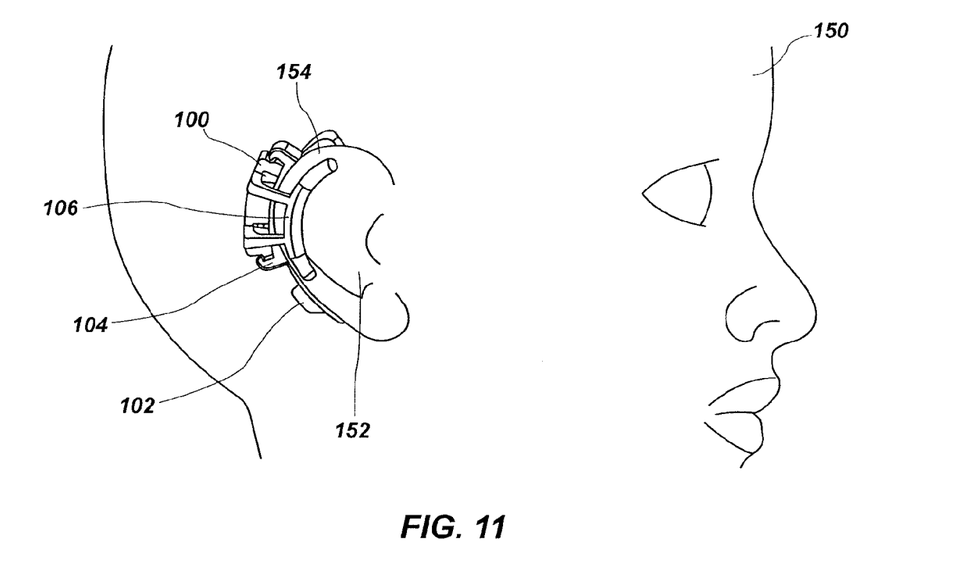
FIG. 11 illustrates a retaining device hereof in use with an ear of a subject in accordance with yet another embodiment of the present disclosure.

FIGS. 11 and 12 illustrates a retaining device 100, which may be similar to any of retaining devices discussed above or below, in use with an ear 152 of a subject. A portion of the retaining device 100 may be adhered to the head 150 of the subject behind the helix 154 of the ear 152, with the retainer portion 106 extending over an outer portion of the helix 154 or other tissue being modified using the retaining device 100. For example, the base portion 102 of the retaining device 100 may be affixed to the subject's head 150 with biocompatible double-sided adhesive tape 156. The tape may be affixed to the base portion 102 and then secured to the subject's head 150 to secure the retaining device 100 in place at least partially behind the subject's ear 152.

FIGS. 13, 14, 15, and 16 illustrate a side view (e.g., lateral side), a perspective view, another side view (e.g., medial side), and yet another side view (e.g., anterior side), respectively, of a retaining device in accordance with another embodiment of the present disclosure, which may, in some embodiments, include similar components, materials, configurations, and methods of forming and/or fitting as the retaining devices discussed above with reference to FIGS. 1 through 12. As shown in FIGS. 13, 14, 15, and 16, the depicted retaining device 500 includes a portion for retaining the ear and a portion for securing the retaining device 500 to the subject's head. For example, the retaining device 500 may include a base portion 502 and a retainer portion 506 that may be coupled at a hinge portion 504.

The base portion 502 of the retaining device 500 may be formed to fit a shape of the skull (i.e., head) of a subject proximate the ear (e.g., proximate the sulcus or the connection of the ear to the subject's head (see, e.g., FIG. 12). For example, the base portion 502 may be formed as a substantially curved shape. An inner portion (e.g., a radially inner portion) of the base portion 502 may be designed to fit complex curvature of the sulcus.

The base portion 502 may include a connection portion 508 for coupling with the retainer portion 506. The connection portion 508 (e.g., at least a portion of a hinge) may be formed on an outer portion (e.g., a radially outer portion) of the curved base portion 502. In some embodiments, the connection portion 508 may form a first portion of a hinge that is complementary to a connection portion 509 on the retainer portion 506 as discussed below in greater detail.

In some embodiments, the base portion 502 may include a protrusion 516 for supporting a portion of the ear (e.g., the auricula). The protrusion 516 may be tapered along the curved base portion 502. For example, the thickness of the protrusion 516 may diminish along the length of the base portion 502 in a direction extending from a lower portion of the base portion 502 configured to be positioned proximate a lower or middle portion of the ear to an upper portion of the base portion 502 configured to be positioned proximate an upper portion of the ear. Stated in another way, the protrusion 516 may include a lower portion (e.g., a portion configured to be positioned proximate to the lobules of the ear) having a first thickness $D_1$ taken in a lateral direction of the retaining device 500 configured to extend between the subject's head and ear and an upper portion (e.g., a portion configured to be positioned proximate to the cymba concha of the ear and/or the helix) having a second thickness $D_2$ taken in the lateral direction. The protrusion 516 may be configured such that second thickness $D_2$ is less than the first thickness $D_1$, thereby forming an angled side surface 520 of the protrusion 516 opposite a mounting surface 512 of the base portion 502.

Such a configuration may enhance the positioning of the base portion 502 between the subject's head and ear and may, in some embodiments, provide additional support to the ear (e.g., for reshaping of the ear) proximate (e.g., at) the sulcus and/or antihelix. For example, the protrusion 516 may act to space the ear proximate the antihelix while the helix is urged toward the subject's head by the retainer portion 506.

The base portion 502 provides a mounting surface 512 for securing (e.g., temporarily securing) the retaining device 500 to the head of the subject (e.g., by the use of an adhesive as discussed above). For example, the base portion 502 may include one or more tabs 510 extending radially outward from the inner portion of the base portion 502 (e.g., at equal intervals along the base portion 502) to form an outer portion of the base portion 502. A portion of the tabs 510 may be smoothed out (e.g., rounded at the distal ends) to prevent the base portion 502 from irritating skin surfaces around the ear.

Referring still to FIGS. 13, 14, 15, and 16, the retainer portion 506 of the retaining device 500 may be configured to retain a portion of the subject's ear (e.g., the helix). For example, the retainer portion 506 may retain the helix proximate to (e.g., against and in contact with) the base portion 502 (e.g., the protrusion 516). The retainer portion 506 may include the connection portion 509 for coupling to the connection portion 508 of the base portion 502.

The retainer portion 506 may include an arm portion 526 (e.g., a curved arm portion) that extend from the connection portion 509. The arm portion 526 may be configured to extend around at least a portion of the helix and/or the scapha of the ear of a subject (e.g., the arm portion 526 may be substantially C-shaped or J-shaped). The arm portion 526 may include an enlarged substantially rounded upper portion 528 that is configured to engage with a portion of the ear. For example, an upper portion of the arm portion 526 (e.g., a portion configured to be positioned proximate to the fossa of the ear and/or the apex of the helix) may include the rounded upper portion 528 that is configured to engage with a portion of the ear proximate the helix and fossa (e.g., at the apex of the helix). A lower portion of the arm portion 526 (e.g., a portion configured to be positioned proximate to the lobules of the ear) may include a curved portion 530 having a substantially constant width $W_1$ (e.g., taken is a direction transverse to the length of the curved portion 530) that is configured to be positioned between the helix and the antihelix of the ear (e.g., along the scapha). The curved portion 530 of the arm portion 526 may be relatively smaller than the enlarged substantially rounded upper portion 528 of the arm portion 526. For example, the width $W_1$ of the curved portion 530 may be smaller (e.g., substantially smaller, for example, less than half of) that a width $W_2$ of the rounded upper portion 528.

An inner portion (e.g., a radially inner portion) of the retainer portion 506 (e.g., the arm portion 526) may be tapered along the length of the retainer portion 506. For example, the thickness of the arm portion 526 may diminish along the length of the retainer portion 506 in a direction extending from a lower portion of the retainer portion 506 configured to be positioned proximate a lower or middle portion of the ear to an upper portion of the retainer portion 506 configured to be positioned proximate an upper portion of the ear. Stated in another way, the arm portion 526 of the retainer portion 506 may include a lower portion (e.g., a portion configured to be positioned proximate to the lobules and/or cymba concha of the ear) having a third thickness $D_3$ taken in the lateral direction and an upper portion (e.g., a portion configured to be positioned proximate to the apex of the helix) having a fourth thickness $D_4$ taken in the lateral direction. The arm portion 526 of the retainer portion 506 may be configured such that the third thickness $D_3$ is less than the fourth thickness $D_4$, thereby forming an angled side surface 532 of the arm portion 526.

In some embodiments, the retainer portion 506 may include a ridge 529 at an outer portion of the arm portion 526. The ridge 529 may extend from the rounded upper portion 528 to a location proximate the connection portion 509 and may be engage the scapha of the subject's ear.

In some embodiments, the arm portion 526 may include one or more extension portions extending therefrom that may be utilized to position another portion of the ear (e.g., portions of the ear proximate the antihelix, the concha, etc.)

Figure 16:
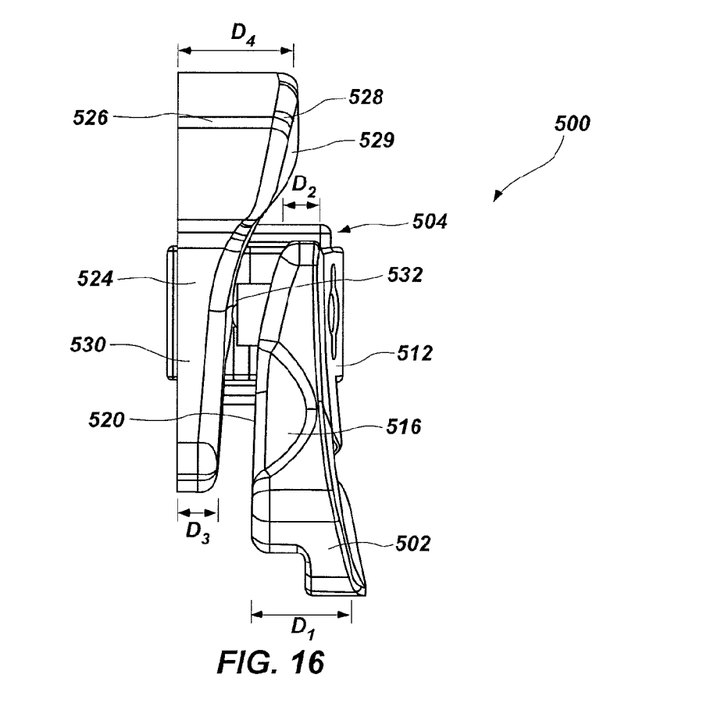
FIG. 16 illustrates yet another side view of the retaining device shown in FIG. 13.
Figure 17:
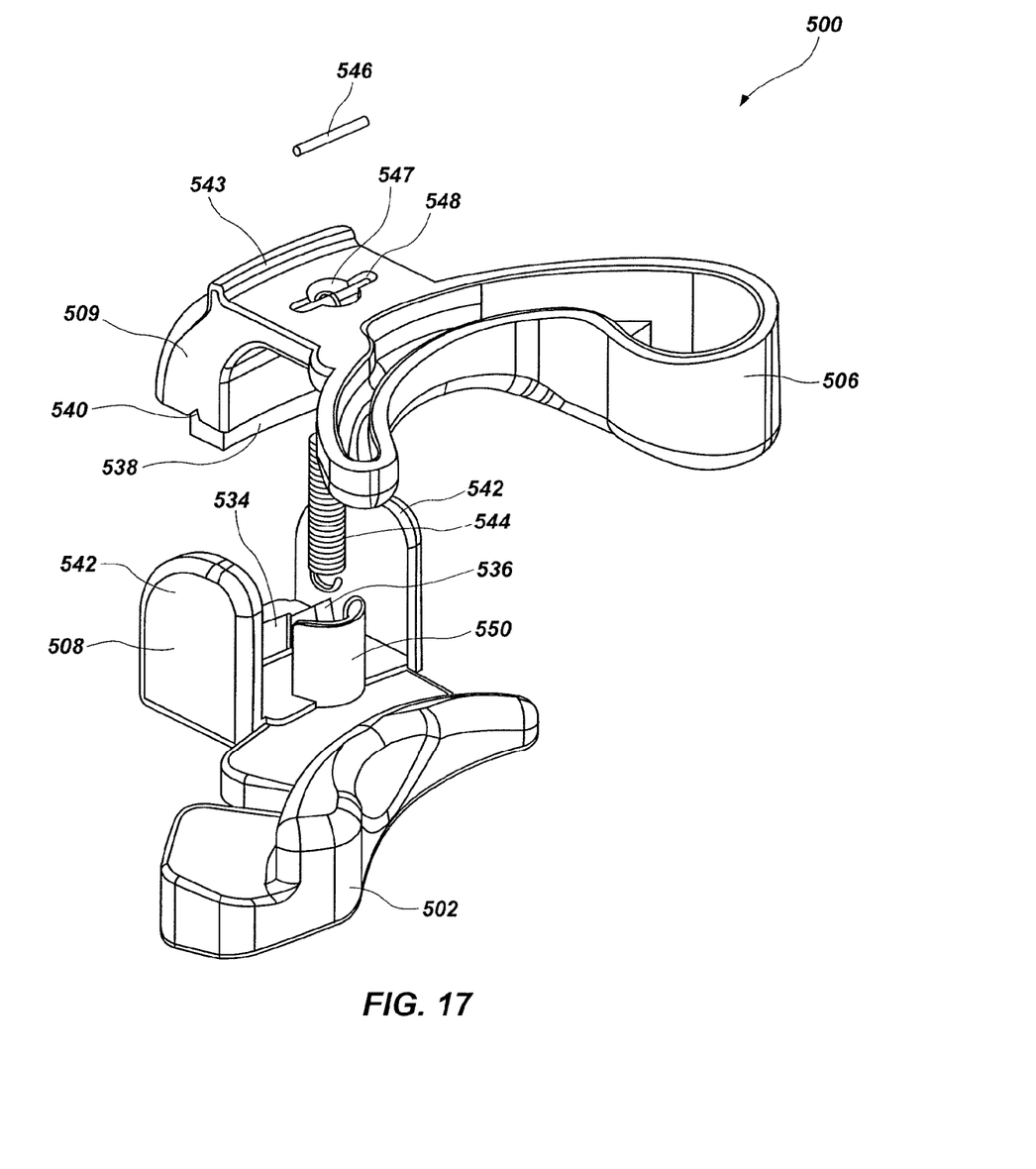
FIG. 17 illustrates an exploded view of the retaining device shown in FIG. 13.
Figure 18:
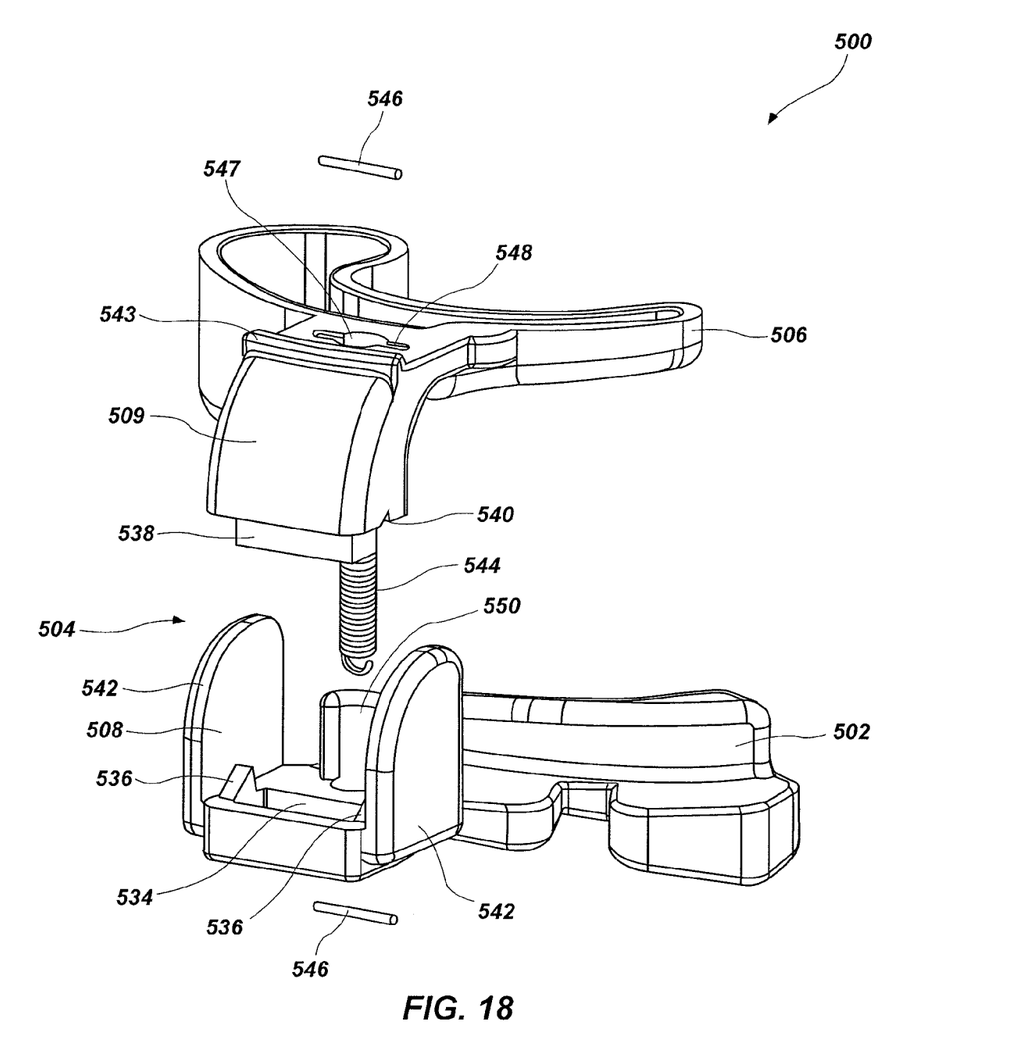
FIG. 18 illustrates another exploded view of the retaining device shown in FIG. 13.

FIGS. 17 and 18 illustrate exploded views of the retaining device 500 shown in FIGS. 13 through 16. As shown in FIGS. 17 and 18, the hinge portion 504 of the retaining device 500 is formed by the connection portion 508 of the base portion 502 and the connection portion 509 of the retainer portion 506. For example, the connection portion 508 of the base portion 502 may include an aperture 534 and one or more protrusions 536 formed on two opposing sides of the connection portion 508. The connection portion 508 of the base portion 502 may include one or more side portions 542 for receiving the connection portion 509 of the retainer portion 506 at least partially therein.

The connection portion 509 of the retainer portion 506 may include a protrusion 538 that is complementary to the aperture 534 in the connection portion 508 (e.g., the protrusion 538 may be received at least partially within the aperture 534) and one or more slots 540 that are complementary to the protrusions 536 of the connection portion 508 (e.g., the protrusions 536 may be received at least partially within the slots 540).

The complementary engagement of the various portions of the connection portion 508 of the base portion 502 and the connection portion 509 of the retainer portion 506 may enable the retaining device 500 to maintain the relative positioning of the base portion 502 and the retainer portion 506 while enabling the base portion 502 and the retainer portion 506 to rotate relative to one another. For example, the retainer portion 506 may rock back and forth on the protrusions 538 that are received in slots 540 in the retainer portion 502. Such movement may enable the retainer portion 506 to rotate about the hinge portion 504 forming an opening between the base portion 502 and the retainer portion 506 enabling the retaining device 500 to be positioned on a subject's ear. For example, a user may apply force (e.g., a pinch) to a portion of the retainer portion 506 proximate the connection portion 509 (e.g., at ridge 543) and to base portion 502 proximate the connection portion 508 to rotate the retaining device 500 about the hinge portion 504 forming an opening between the base portion 502 and the retainer portion 506 such that the retaining device 500 may be positioned on a subject's ear.

In some embodiments, the retaining device 500 may include a biasing feature 544 that may bias and/or adjust the position of the retainer portion 506 relative to the base portion 502. For example, the biasing feature 544 that may bias the retaining device 500 in an initial or closed position with the base portion 502 and the retainer portion 506 positioned proximate (e.g., adjacent) each other (e.g., as shown in FIG. 16). The biasing feature 544 may act to hold the retainer portion 506 in position, which, in turn, holds the subject's ear in a selected position. As depicted, the biasing feature 544 may comprise a tension spring that is coupled to the base portion 502 and the retainer portion 506 of the retaining device 500 and extends through openings 547 formed in the base portion 502 and the retainer portion 506. One or more pins 546 may be received within one or more grooves 548 formed in the base portion 502 and the retainer portion 506 to couple the biasing feature 544 to the retaining device 500. In other embodiments, the biasing feature may comprise other types of springs (e.g., torsion, compression, etc.) or any other suitable biasing device.

In other embodiments, the retaining device 500 may include an adjustable feature rather than or in additional to the biasing feature 544 at the hinge portion 504. For example, the hinge portion 504 may comprise an adjustable feature (e.g., a fastener such as a screw) that may be utilized to adjust the relative positioning of the base portion 502 and the retainer portion 506.

In yet other embodiments, the hinge portion 504 may comprise a living hinge and one of the biasing or adjustment features discussed above.

In some embodiments, a portion of the retaining device 500 (e.g., the base portion 502) may include a shield 550 to protect the subject's ear from contact with the biasing feature 544.

As discussed above, the complementary engagement of the various portions of the connection portion 508 of the base portion 502 may enable the base portion 502 and the retainer portion 506 to rotate relative to one another. In some embodiments, the complementary engagement of the various portions of the connection portion 508 of the base portion 502 in unison with the biasing feature 544 may enable the base portion 502 and the retainer portion 506 to translate relative to one another. For example, the protrusion 538 of the retainer portion 506 may be at least partially removed from the aperture 534 in the base portion 502 (e.g., as the retaining device 500 is position on a subject's ear. The biasing feature 544 may act to urge the base portion 502 and the retainer portion 506 back together once the force applied to the retaining device 500 to separate the base portion 502 and the retainer portion 506 is removed (e.g., once the retaining device 500 is fitted on the subject). For example, the biasing feature 544 will urge the protrusion 538 of the retainer portion 506 back into the aperture 534 in the base portion 502. In some embodiments, the side portions 542 may act to guide the retainer portion 506 back into engagement with the base portion 502.

In use, for example, a physician will measure the subject to gather pertinent data, such as sulcus height, curvature, and desired finished angle, and note any other deformities that are to be treated. For example, as described in the above incorporated by reference patent application, WO 2011/129900 A2, a cartilage structure may be treated with a laser so as to stimulate chonrdogenesis (i.e., the forming or reforming of cartilage structures) and encourage cartilage growth. After treatment, a retaining device (e.g., retaining devices 100, 200, 300, 400, 500) may be attached to the ear of the subject to position the ear while the cartilage of the ear is formed and/or reformed. The base portion 102, 202, 302, 402, 502 of the retaining device 100, 200, 300, 400, 500 may be adhered to the subject's head and/or ear.

In some embodiments, and as discussed above, the physician may select and/or customize the retaining device 100, 200, 300, 400, 500 or one or more of its components to position the subject's ear in the desired position. The retainer portion 106, 206, 306, 406, 506 may be positioned and/or attached to the base portion 102, 202, 302, 402, 502 and spacer portion 104, 204, 304, 404 (where implemented) before, during, or after the base portion 102, 202, 302, 402, 502 is secured to the subject's head.

The retaining devices 100, 200, 300, 400, 500 can remain on the subject head for several days or weeks depending upon subject comfort and success.

In some embodiments, one or more components of the retaining devices 100, 200, 300, 400, 500 may include coating to reduce irritation to the subject skin (e.g., through rubbing and/or abrasion). For example, one or more components of the retaining devices 100, 200, 300, 400, 500 may include a low-friction coating (e.g., silicon, foam rubber, etc.).

Once being apprised of the instant retaining devices, one of ordinary skill in the art will be readily able to make (e.g., by injection molding) the device.

What is claimed is:

1. A retaining device for positioning and retaining an ear of a subject in a desired position relative to the subject's head useful as part of a treatment to alter the shape of an ear of the subject, the retaining device comprising:
    a first portion configured to be secured to the subject's ear and to the subject's head, wherein the first portion comprises a base portion formed to fit a shape of the subject's head proximate the ear for at least partial adherence of the retaining device to the subject's head, the base portion being further structured to space a portion of the ear from the subject's head while permitting the ear's helix to displace toward the subject's head; and
    a second portion, coupled to the first portion by a hinge portion, configured to position and retain the helix of the subject's ear in a desired position relative to the subject's head; wherein:
    the second portion comprises a retainer portion configured to extend along a portion of the subject's ear's helix to retain the portion of the helix proximate to the subject's head;
    a protrusion of the base portion comprises a first tapered surface having a first thickness at a lower portion of the protrusion in a lateral direction configured to extend between the subject's head and ear that is greater than a second thickness at an upper portion of the protrusion taken in the lateral direction, the second thickness being operable to space the lobule of the subject's ear apart from the subject's skull by a first distance that is greater than a second distance by which the tapered surface spaces a middle portion of the ear's anti-helix apart from the skull;
    the retainer portion comprises a second tapered surface having a first thickness at a lower portion of the retainer portion in the lateral direction that is less than a second thickness at an upper portion of the retainer portion taken in the lateral direction; and
    the first tapered surface is disposed generally in parallel with the second tapered surface to form a gap in which to confine a portion of the ear, the gap being oriented to slope medially in a vertical direction and to urge the apex of the helix toward the subject's skull.

2. The retaining device of claim 1, further comprising:
    adhesive carried on the base portion for adhering the retaining device to the subject's head.

3. The retaining device of claim 2, wherein the retainer portion is configured to extend along a perimeter portion of the subject's ear's helix to retain the perimeter portion of the subject's helix proximate to the subject's head.

4. The retaining device of claim 3, wherein the retainer portion comprises a curved shape configured to engage with the subject's ear proximate at least one of the scapha and the helix of the subject's ear.

5. The retaining device of claim 4, wherein the curved shape of the retainer portion includes an enlarged upper end portion configured to engage with the subject's ear proximate the apex of the helix of the subject's ear.

6. The retaining device of claim 1, wherein a radially inner portion of the base portion comprises a curved shape structured to fit a complex curvature of the sulcus of a subject's ear, the curved shape comprising an area with concave curvature structured to partially wrap a base of the subject's ear.

7. The retaining device of claim 6, wherein the protrusion is configured to support the auricula of the subject's ear proximate the sulcus.

8. The retaining device of claim 1, wherein the first portion and the second portion rotate relative to one another about the hinge portion between a first retaining position for retaining the subject's ear proximate the subject's head and a second open position for placing the retaining device on the subject's ear.

9. The retaining device of claim 8, wherein the hinge portion is biased in the first retaining position.

10. The retaining device of claim 9, wherein the hinge portion comprises a tension spring.

11. The retaining device of claim 8, wherein the hinge portion of the retaining device is configured to move to the second open position responsive to a pinching force from a user.

12. The retaining device of claim 1, wherein the base portion is flexible so as to be configurable to at least partially conform to the curvature of the subject's head.

13. The retaining device of claim 12, wherein the second portion is removably connected to the first portion.

14. The retaining device of claim 1, wherein the second portion comprises two arms extending from the first portion to cross over the subject's ear's helix and a retainer coupled to a distal end of each of the two arms, the retainer being formed to extend approximately in parallel with, and along a portion of the subject's helix, the arms being biased to urge the retainer and helix toward the base portion.

15. The retaining device of claim 1, wherein the second portion comprises at least two retainers extending from the first portion, each retainer of the at least two retainers having a respective and individual cantilevered portion configured to extend laterally from a cantilever anchor on the first portion across a portion of a subject's ear's helix to dispose retaining structure on a lateral side of the ear.

16. The retaining device of claim 15, wherein the at least two retainers are slidably coupled to the first portion to permit a change in anchored position of each of the at least two retainers with respect to the first portion.

17. The retaining device of claim 15, wherein at least one retainer of the at least two retainers comprises a wire extending therefrom, the wire being configured and arranged to extend across the lateral surface of the ear to apply a force to a portion of the ear.

* * * * *